United States Patent [19]
Baylor et al.

[11] Patent Number: 5,412,465
[45] Date of Patent: May 2, 1995

[54] METHOD FOR VERIFICATION OF CONSTITUENTS OF A PROCESS STREAM JUST AS THEY GO THROUGH AN INLET OF A REACTION VESSEL

[75] Inventors: Lewis C. Baylor, North Augusta; Bruce R. Buchanan, Aiken, both of S.C.; Patrick E. O'Rourke, Martinez, Ga.

[73] Assignee: The United States of America as represented by the United States Department of Energy, Washington, D.C.

[21] Appl. No.: 100,162

[22] Filed: Aug. 2, 1993

[51] Int. Cl.$^6$ ............................................. G01J 3/44
[52] U.S. Cl. ................................. 356/301; 356/317; 356/319; 110/186; 364/498
[58] Field of Search ............... 356/301, 300, 303, 319, 356/326, 410; 364/498, 497; 110/185, 186, 188, 235, 237; 436/104

[56] References Cited

U.S. PATENT DOCUMENTS

| | | | |
|---|---|---|---|
| 4,620,284 | 10/1986 | Schnell et al. | 364/498 |
| 4,666,696 | 5/1987 | Shultz | 423/659 |
| 5,002,397 | 3/1991 | Ingrum et al. | 356/407 |
| 5,014,217 | 5/1991 | Savage | 364/498 |
| 5,059,790 | 10/1991 | Klainer et al. | 250/227.21 |
| 5,295,448 | 3/1994 | Vickery | 110/235 |
| 5,311,444 | 5/1994 | Ohta | 364/498 |

OTHER PUBLICATIONS

L. D. Hoffland et al., "Spectral Signatures of Chemical Agents and Stimulants," *Optical Engineering* vol. 24, No. 6 (Nov./Dec. 1985), pp. 982–984.

Primary Examiner—F. L. Evans
Assistant Examiner—Jason D. Eisenberg
Attorney, Agent, or Firm—Brian R. Tumm; Harold M. Dixon; William R. Moser

[57] ABSTRACT

A method for validating a process stream for the presence or absence of a substance of interest such as a chemical warfare agent; that is, for verifying that a chemical warfare agent is present in an input line for feeding the agent into a reaction vessel for destruction, or, in a facility for producing commercial chemical products, that a constituent of the chemical warfare agent has not been substituted for the proper chemical compound. The method includes the steps of transmitting light through a sensor positioned in the feed line just before the chemical constituent in the input line enters the reaction vessel, measuring an optical spectrum of the chemical constituent from the light beam transmitted through it, and comparing the measured spectrum to a reference spectrum of the chemical agent and preferably also reference spectra of surrogates. A signal is given if the chemical agent is not entering a reaction vessel for destruction, or if a constituent of a chemical agent is added to a feed line in substitution of the proper chemical compound.

20 Claims, 2 Drawing Sheets

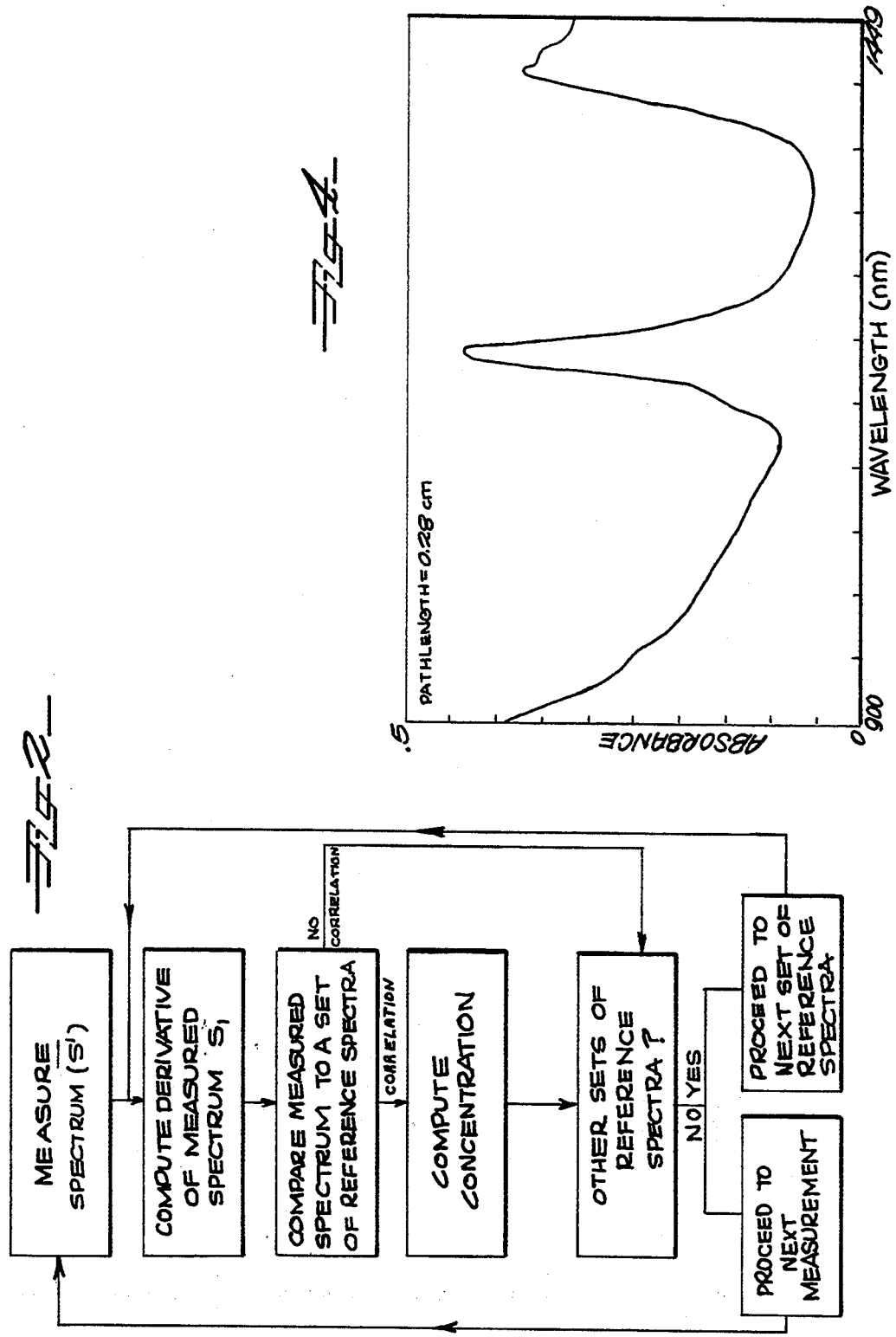

METHOD FOR VERIFICATION OF CONSTITUENTS OF A PROCESS STREAM JUST AS THEY GO THROUGH AN INLET OF A REACTION VESSEL

BACKGROUND OF THE INVENTION

1. Field of the Invention

The present invention relates to a method for verification of the constituent chemical compounds of a process stream, that is, for verifying that a chemical substance that should or should not be present in a process stream is in fact present or not present, respectively. In particular, the invention relates to verifying the presence of a chemical warfare agent to be destroyed in a destruction facility, and verifying the absence of such substances in a facility not intended for producing chemical warfare agents. The United States Government has rights in this invention pursuant to Contract No. DE-AC09-89SR18035 between the U.S. Department of Energy and Westinghouse Savannah River Company.

2. Discussion of Background:

The U.S. and other nations have large stockpiles of chemical warfare agents, including the so-called "nerve gases": HD (mustard gas), GA (tabun), GB (sarin), etc. Some stocks are outdated and must be destroyed; others are scheduled for destruction to comply with treaty requirements. Agents shipped to a destruction facility could conceivably be diverted and replaced by simulants or surrogates. Therefore, it is important to verify that "declared" agents, that is, agents for which claims are made that they are a constituent being introduced into a destruction facility, are actually introduced and are being destroyed. On-site inspection may be difficult to arrange and only partially effective. Furthermore, nerve gas agents are lethal in extremely small quantities, so any testing procedure must minimize the possibility of human exposure.

From time to time, other hazardous substances that present verification problems may be scheduled for destruction. Such substances include common pesticides and insecticides, and hazardous byproducts from industrial processes.

Related to the problem of verifying the destruction of chemical warfare agents, is the problem of verifying that such agents are not being produced. Common phosphene-based pesticides are chemically related to nerve gas agents and are manufactured by similar processes. For example, the pesticide diazinon is similar to the nerve gas agent GB (sarin). A diazinon manufacturing facility can be converted to GB production in a few weeks. In some cases, it is important to verify that a legitimate pesticide plant is not being used to manufacture nerve gas agents. Here, rather than the absence of a hazardous substance among the constituents that might signal a diversion, it is the presence of a constituent of a hazardous substance that might signal that hazardous substances are being made.

It is well known to analyze the exhaust gases of an incinerator as a check on its efficiency. For example, Schultz (U.S. Pat. No. 4,666,696) describes a process for the destruction of nerve gases and other cholinesterase inhibitors by molten metal reduction in a furnace. The exhaust gases are analyzed for the presence of the agent(s) being destroyed and returned to the furnace if not free of the agents. However, verifying the identity of a substance just before it is introduced into an incinerator or other destruction facility has not been done.

There is a need for a method for verifying the identity of a substance before it is introduced into a destruction facility, or, alternatively, to verify that a substance is absent from a production facility.

SUMMARY OF THE INVENTION

According to its major aspects and broadly stated, the present invention is a method for verifying the constituent chemical compounds of a process stream for the presence or absence of a substance of interest to validate the process. The term "validate" as used herein means to verify that a substance that should not be present in the stream is not present, and/or that a substance that should be present, is present. The goal of validation is to confirm that the process, is not producing hazardous compounds through error or deception or that hazardous compounds are not being intentionally or negligently diverted from a process intended to destroy them.

The method is applied in a facility where chemical processes take place such as in a reaction vessel. The constituents of the chemical processes are fed into the reaction vessel through an inlet. The method, then, includes the steps of directing a light beam through said constituent chemical substance in the inlet just as it is entering said reaction vessel; measuring an absorption, Raman or fluorescence spectrum of the constituent compound from said light beam after it emerges from passing through the constituent; comparing the spectrum to a set of reference spectra for that constituent to determine a match for the measured spectrum; and emitting a signal to confirm the constituent chemical compound is entering said reaction vessel.

When the chemical process is designed to destroy a hazardous chemical, the process verifies that it has actually passed through the inlet and into the interior of the reaction vessel and has not been substituted, for example, by a surrogate chemical compound. When certain chemical compounds that can be used in a chemical process otherwise intended for making a commercial product are replaced by others that make chemical warfare agents, for example, the present process can detect that the substitution has taken place, or the present method can be used by the facility operator to confirm that the substitution has not taken place.

An important feature of the present invention is the location of the sensor used for the measurement with respect to the reaction vessel, namely, in close proximity to it and preferably just as the constituents pass from the inlet into the reaction vessel so that no opportunities to substitute surrogates are available after the measurement is made. The method of the present invention might be used to comply with regulatory requirements for materials such as Schedule II chemicals (chemicals that can be used for chemical weapons manufacture), hazardous substances subject to reporting and inventory requirements, and so forth.

Another important feature of the present invention is that it does not provide more information than needed; it simply provides either confirmation that the process stream does not include improper constituents or that it does. Therefore, the information needed to comply with any applicable reporting requirements is obtained without divulging proprietary information about the process, which is a significant advantage because it overcomes that objection to compliance.

Yet another important feature of the invention is that, by using optic fibers to transmit light to and from the inlet where the light beam passes into the constituent of interest, the analysis can be done quickly—almost real time—and without taking a sample and incurring thereby the handling and disposal problems associated with samples.

Also, the accuracy of the analysis is another important feature of the present invention. Because some constituents can be simulated by surrogates, accuracy in verification of the material is essential. Optical spectrum measurements can be used to discern fine differences between chemical compounds and computer comparison techniques can be programmed to look for signature differences between surrogates and the real chemical constituent.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 2 is a flow chart of a part of a method according to a preferred embodiment of the present invention for determining the concentration of a substance of interest in the facility of FIG. 1;

FIG. 4 is a graph of the absorbance of HD (mustard gas), measured in the facility according to the schematic of FIG. 3.

DETAILED DESCRIPTION OF A PREFERRED EMBODIMENT

Figure 1:
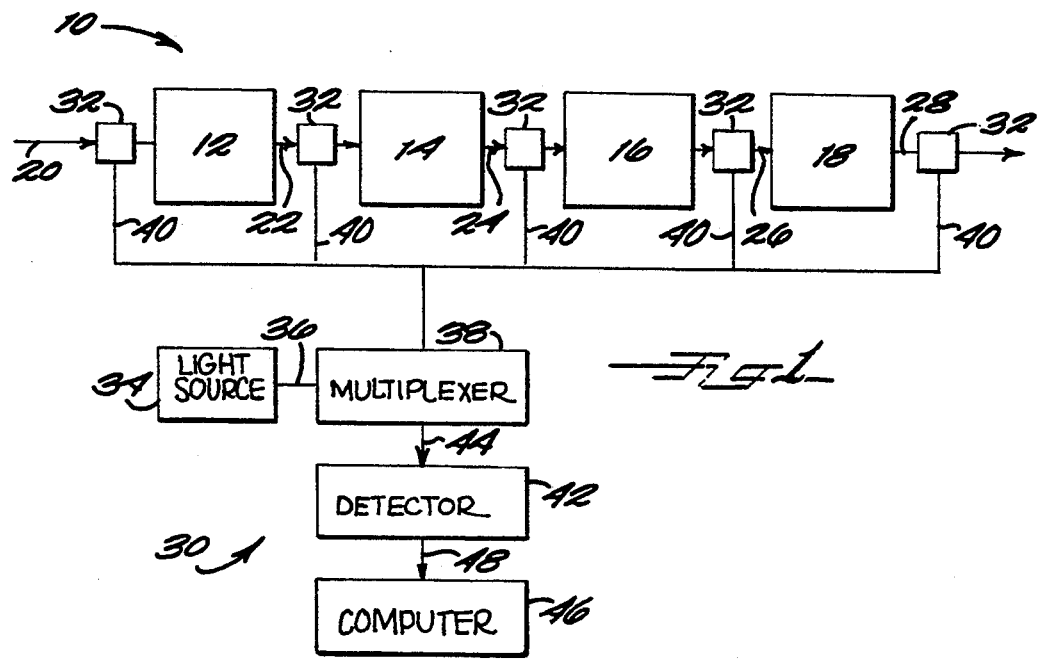
FIG. 1 is a schematic view of a facility having apparatus for implementing the method according to a preferred embodiment of the present invention.

Referring now to FIG. 1, there is shown a representation of a laboratory or industrial facility 10, having a series of process vessels 2, 14, 16, 18 such as tanks, evaporators, and the like, joined by piping. Material in liquid or slurry form flows through a conduit 20 into vessel 12, then from vessel 12 through a conduit 22 to vessel 14, through a conduit 24 to vessel 16, and through a conduit 26 to vessel 18 before exiting facility 10 via a conduit 28. Typical industrial, chemical processes such as precipitating, mixing, storing, evaporating, and reacting, may take place in one or more of the vessels. Facility 10 may, if needed, have more or fewer process vessels such as vessels 12, 14, 16 and 18. Air, fuel, and process materials may be added to the vessels through input lines; byproducts may be removed through output lines (not shown). Devices such as quenchers, scrubbers, filters, demisters, input and output valves, sensors and so forth may be positioned at various locations in facility 10, depending on the nature of the process.

The process that takes place in facility 10 is not part of the present invention nor is any particular step or sequence of steps in that process crucial to the practice of the present invention. Facility 10 represents a generalized facility for the production of industrially or commercially useful products, but particularly one that uses ingredients that could be used for production of compounds useful as chemical warfare agents, and one that could be converted to the production of chemical warfare agents such as a commercial pesticide manufacturing plant. Alternatively, facility 10 may be a facility for the destruction of chemical warfare agents, having a reaction vessel such as an incinerator for rendering such agents harmless.

Facility 10, whether a facility for production of commercial products or for the destruction of harmful ones, has a process that must be validated. As noted above, the term "validate" means to verify that a substance that should be present in fact is present, and that a substance that should not be present, is not present. Also, a "production facility" will refer to a facility that makes industrially or commercially useful products. "Destruction facility" will be used to refer to a facility where chemical warfare agents are to be destroyed. It will, however, be clear that hazardous compounds other than chemical warfare agents are of concern and that a destruction facility might be set up for destroying excess or out-of-date supplies of commercially useful chemicals that are also toxic in such cases where the operators of that facility want to assure themselves that the materials being destroyed are those that are earmarked for destruction. Thus, for a production facility, "validate" means to verify that materials associated with the production of chemical warfare agents—including the agents themselves—are not being made by facility 10. Conversely, in a destruction facility, "validate" means to verify that such agents (and not simulants or surrogates) are fed into a reaction vessel for destruction.

According to a preferred embodiment of the present invention, a method for validating the process that takes place in facility 10 is implemented with an apparatus indicated by reference character 30 in FIG. 1. Apparatus 30 includes at least one sensor positioned at a location where process validation is desired. Such locations are indicated by a plurality of sensors 32, positioned in conduits 20, 22, 24, 26 and 28. Sensors 32 are any type of optical sensor for optical spectrum measurements, preferably sensors adapted for use in the process environment. Suitable sensors include, but are not limited to those described in commonly-assigned U.S. Pat. No. 5,039,224 (Self-Referencing Optical Probe) and U.S. Pat. No. 5,131,746 (On-Line Process Control Monitoring System), and commonly-assigned and recently filed patent applications Ser. No. 07/843,334 (Light Absorption Cell Combining Variable Path and Length Pump) and Ser. No. 08/056,390 (Fiber Optic Probe Having Fibers With Endfaces Formed For Improved Coupling Efficiency), the disclosures of which are incorporated herein by reference. If desired, additional sensors (not shown) may be placed in process vessels 12, 14, 16, 18, and in various input and output lines of facility 10. If facility 10 is a destruction facility, sensors should be placed in any input line leading to a reaction vessel that will destroy the chemical compound. In a production facility, a sensor can be also placed in any line leading to a reaction vessel. Because there is likely to be more than one process vessel in a production facility, a sensor can be placed in every input line, but at least every one where an additional constituent could be added to the process stream.

A light beam from a source 34 is transmitted by an optical fiber 36 to a multiplexer 38. Multiplexer 38 is in optical communication with sensors 32 via a plurality of optical fiber assemblies 40, each assembly 40 having a transmission fiber and a return fiber for transmitting light to and from sensors 32, respectively. If convenient, separate multiplexers may be provided for the transmitting and receiving fibers of optical fiber assemblies 40. The output of multiplexer 38 is fed to a detector 42 via an optical fiber 44.

When absorption spectra are to be measured, light from source 34 is transmitted through the process stream via the transmission and return fibers of assemblies 40.

When fluorescence or Raman spectra are to be measured, light from source 34 is directed into the process stream by the transmission fibers of assemblies 40. In fluorescence, the constituents of the stream are excited by absorbing the light and emit light of characteristic frequencies. The Raman effect is observed in the scattering of light as it passes through a medium. The scattered light undergoes a change in frequency and a random alteration in phase due to a change in the rotational or vibrational energy of the scattering molecules. The emitted light (fluorescence spectra) or scattered light (Raman spectra) is fed to multiplexer 38 by the return fibers of assemblies 40.

Detector 42 includes a spectrophotometer adapted for measuring optical spectra in any convenient wavelength range, including Raman, fluorescence, ultraviolet-visible (UV-Vis), infrared (IR) and near infrared (near-IR). Detector 42 preferably includes a fast scan spectrophotometer with an analog-to-digital converter for digitizing the light signals received from sensors 32. Detector 42 may be capable of measuring more than one type of spectrum, such as Raman spectra for identifying a substance of interest and near-IR spectra for determining the concentration of the substance.

The output of detector 42 is passed to a computer 46 by a connecting link 48. Computer 46 analyzes the data generated by detector 42. Computer 46 may also control the operation of multiplexer 38 and facility 10. Alternatively, a separate computer system (not shown) may control the processing of materials in facility 10.

The components of apparatus 30 are adapted for use in the operating environment of facility 10. Light source 34, multiplexer 38, detector 42 and computer 46 may be located remotely or at the site of facility 10. All instrumentation used with apparatus 30 is rugged and durable, with low maintenance requirements to minimize personnel exposure to any hazardous or potentially hazardous materials at the site. Penetrations into facility 10, such as for installation of sensors 32 and optical fiber assemblies 40, should be durable and leak-free.

Light source 34 may be a broad-band radiant energy source such as a quartz-halogen lamp or a light-emitting diode. Optical fibers 36, 40, 44 are any optical fibers that are adapted for use in the operating environment of facility 10, such as polymer-clad silica fibers with good light-carrying capacity.

Computer 46 is preferably a general purpose computer programmed for analyzing the spectral data received from sensors 32. Computer 46 uses stored algorithms to process the digitized information received from detector 42 and determine whether a substance of interest is/is not present in facility 10, and if present, the concentration of the substance. The results of these computations may be displayed in any convenient manner, including visually, by recording using a printer/plotter, used to activate an audio/visual alarm system, or transmitted to a remote location for viewing.

Depending on the nature of the process taking place in facility 10, reference spectra ("spectral signatures") of chemical warfare agents, certain materials used in the production of such agents, and simulants and surrogates thereof, are stored in computer 46. These known spectra are used to validate facility 10. By way of example, Schedule II chemicals and other materials are subject to regulatory controls and accounting requirements. Many common, widely-used materials are Schedule II chemicals, including ethylene glycol (a starter material for HD (mustard gas)). In a phosphene-based manufacturing plant, fluorine is present if and only if GB (sarin), and cyanide if and only if GA (tabun) are being manufactured. Chemical warfare agents whose signatures may be available include a variety of compounds, including but not limited to those known as GA (tabun), GB (sarin), GD (soman), HD (mustard gas), CN (chloracetophenone), DIMP (diisopropylmethyl phosphonate) and DMMP (dimethylmethyl phosphonate).

Computer 46 is programmed with a model that correlates the measured spectra from sensors 32 with the reference spectra stored in computer 46. Computational analyses may include Partial Least Squares, Principle Component Regression (PCR), Classical Least Squares and Multiple Linear Regression, and other analyses known to those skilled in the art.

As an example, the absorbance spectrum A(v) is computed from the measured intensity of light transmitted through a sensor 32:

$$A(v) = -\log 10(I(v)/I_0(v)),$$

where $I(v)$ is the measured intensity of light at frequency v, and $I_0(v)$ is the blank intensity measurement. A library search, using techniques well known in the art of spectroscopy, is performed to determine whether or not a substance of interest is present. Thus, the wavelengths, amplitudes and widths of the peaks in the measured spectrum may be correlated to those of a reference spectrum. If the two spectra are similar, that substance is present in the sample. Preferably, a type of spectrum having a high qualitative information content is used for this portion of the analysis. Raman spectra, for example, are frequently used to identify compounds. Depending on the nature of the process taking place in facility 10, computer 46 may contain data on 5–10 or even fewer compounds, however, more data may be stored if needed.

If a correlation is found, the measured spectrum may be analyzed to determine the concentration of the substance. Raman spectra are frequently less useful for quantitative analysis than other types of spectra such as UV-Vis, IR or near-IR, therefore, the latter are preferred for this step of the analysis.

Alternatively, the concentration of the substance of interest is determined and compared to a preselected value. The substance is said to be "present" in the process stream if the measured concentration is greater than the preselected value, and substantially "absent" from the process stream if the concentration is no greater than the preselected value.

Using PCR, the method of the present invention is implemented generally as follows:

1. Measure the spectra of a set of calibration samples having a range of concentrations of a substance of interest to obtain S, a set of vectors that represents the spectra and their variations with the concentration. The measurements preferably cover the range of concentrations that could be encountered during operation of facility 10.
2. Take a derivative, S', of S.

3. Decompose the set of S' into a set of orthonormal vectors V, where V represents spectral variations contained in the set S'.
4. Compute the dot product of S' with V:

$$E = S' \cdot V.$$

5. The concentration is related to E by the equation $C = f(E_i)$. For many substances of interest, C is a linear function of E:

$$C = \sum_i A_i E_i + B,$$

where C is the concentration, and $A_i$ and B are constants. The constants $A_i$ and B are derived from a least squares fit of the computed values of $E_i$ versus concentration. For some substances, $f(E_i)$ may assume some other form such as a polynomial, exponential, or other type of function. Therefore, $f(E_i)$ is best determined by a modest amount of observation and experimentation for each particular substance.

Once the constants $A_i$, and B are known for a substance, a process stream can be validated by the procedure diagrammed in FIG. 2:

1. Position a suitable sensor in facility 10, in a location where the process stream is to be validated.
2. Using the sensor, measure the spectrum of the process stream.
3. Compute a derivative of the measured spectrum. If desired, second and higher-order derivatives of the measured spectrum may also be computed and used in the analysis.
4. Compare the measured spectrum to a stored reference spectrum or set of reference spectra. If the measured spectrum correlates with the reference spectrum, proceed to Step 5 to determine the concentration of that substance.

If there is no correlation, that substance is not present in facility 10 and the analysis is terminated. Proceed to the next spectrum measurement, or, where more than one reference spectrum is provided, compare the measured spectrum to the next reference spectrum to determine whether additional substances are present in facility 10.

The measured and reference spectra may be compared directly. Alternatively, the first derivatives of the spectra, or higher-order derivatives if desired, may be compared instead of or in addition to the spectra themselves to determine whether or not there is a correlation. If desired, steps 3 and 4 may be reversed, that is, the measured and reference spectra may be compared directly before computing the derivative(s) of the measured spectra.

If facility 10 is a destruction facility, the presence of the substance in the process stream provides assurance that the substance will be destroyed. Thus, an alarm signal may be generated if no correlation is found, i.e. the substance is not present. Conversely, in a production facility, a correlation indicates that an improper substance is present in the facility. Therefore, an alarm may be generated upon finding a correlation.

5. Compute $E_i$.
6. Compute the concentration using the equation $C = \Sigma A_i E_i + B$, where $A_i$ and B are known constants for the substance.

Calibration data for one or more substances of interest may be stored in computer 46. Therefore, the procedure described above is used to compare a single measured spectrum with as many reference spectra as are needed for the particular application. Once a substance of interest is determined to be present at a sensor location in facility 10, the concentration of that substance is found using the appropriate constants $A_i$ and B. It will be evident that the concentration, together with the flow rate of the process stream, may be used to compute the amount of the substance entering facility 10.

To minimize the possibility of diversion, sensors 32 are preferably positioned in the flow path of materials within facility 10. Where facility 10 is a production plant, sensors 32 may be used solely to provide data concerning the presence/absence of substances such as Schedule II chemicals. Alternatively, sensors 32 may be incorporated into an overall process control system for facility 10, and provide data as to the concentrations of all chemicals of interest.

Spectra may be measured from each sensor 32 at regular intervals, such as every 5 or 10 minutes or every hour. Each measurement requires only a few seconds, so a single multiplexer 38, detector 42 and computer 46 may be used to collect data from a number of sensors 32. Alternatively, to minimize the possibility of diversion of materials when the measurement schedule is known or determinable, measurements may be taken at random intervals. Computer 46 can easily be programmed to activate data collection at random or pseudo-random intervals by using well known techniques such as random number generator routines.

The transmitted light intensity I(v), used to compute the absorbance A(v), can be obtained by the appropriate choice of sensor 32 for a particular application. However, in some situations it may be difficult or impossible to obtain reliable measurements of the blank intensity $I_0(v)$. If the substance of interest is photoreactive, or capable of forming a photoreactive complex with a photoreactive indicator dye, the invention may be implemented using self-referencing spectrophotometry as described in our recently filed and commonly assigned patent application Ser. No. 07/957,133 (Self-Referencing Spectrophotometric Measurements), the disclosure of which is incorporated herein by reference.

Self-referencing spectrophotometry relies on the photoreactive properties of either the substance itself, or a photoreactive complex made of the substance and a photoreactive indicator. The change in the intensity of light transmitted through a sample over a period of time is measured as the photoreactive substance (or photoreactive complex) decomposes to a product substance. The first measured spectrum is used as the blank intensity $I_0(v)$ for the subsequent measurements. The differences between the successive spectra correlate with the initial concentration of the substance. Using a known exposure time and a known delay time between measurements, the concentration of the substance of interest can be derived from the differences between mathematical representations of the spectra.

Measurements may be taken until no more changes are observed from one spectrum to the next succeeding spectrum, indicating that decomposition of the photoreactive component of the sample is complete. Often, however, the photolysis rate is slow, or is complicated by secondary photolysis reactions that occur after substantial decomposition products have formed. It is desirable, therefore, to be able to predict the concentration from the first few spectral measurements. The rate of disappearance of the photoreactive material depends not only on the initial concentration of this material but also on the amount of light falling on the sample, the sample matrix, its temperature and a variety of other factors. It is impractical to use the rate of disappearance as a measurement of the initial concentration of photosensitive material. However, the rate of disappearance is an exponential function of the following form:

$$C(t) = C_0(1 - \exp^{-bt})$$

where $C(t)$ is the concentration at time t, $C_0$ is the initial concentration, and b is a rate constant. This equation can be fitted to data derived from the set of spectra constructed from the photolysis measurements to yield $C_0$ because, as discussed above, concentration is proportional to absorbance. The data fitted to the exponential equation can be as simple as a single wavelength of an isolated absorbance band. However, a more reliable and general technique makes use of calibration data obtained by measuring standard samples having known concentrations of the substance(s) of interest. These data are analyzed by any of a number of techniques such as PCR and Partial Least Squares.

PCR and Partial Least Squares both model spectral data sets by constructing orthogonal vectors to describe the variance between the spectra in the set. In PCR analysis, the vectors are chosen to minimize the error in the spectral data. An unknown spectrum is decomposed to eigenvalues corresponding to each of the principal component regression vectors. To build a model, the eigenvalues of the spectra in a calibration data set are correlated with the known concentrations by any of a number of suitable methods such as Multiple Least Squares, substantially as described above for reference spectra stored in computer 46. Once computed, the eigenvalues of this model can be related to unknown concentrations through well known techniques such as multiple linear regression.

Partial Least Squares analysis assumes a linear relationship between the data and the concentrations. An unknown spectrum is analyzed by computing likenesses between the spectrum and the orthogonal vectors of the calibration data set, then summing the contribution to the concentration from each of the vectors. Spectrum residuals are computed by subtracting the likenesses of the vectors from the original spectrum. The number of vectors used to describe a given chemical system is determined by minimizing the predicted error of a set of spectra with known concentrations. Whether PCR, Partial Least Squares, or some other technique is used depends on the nature of the substance to be detected, the instrumentation used with facility 10, and such other factors as will be evident to those of ordinary skill.

Figure 3:
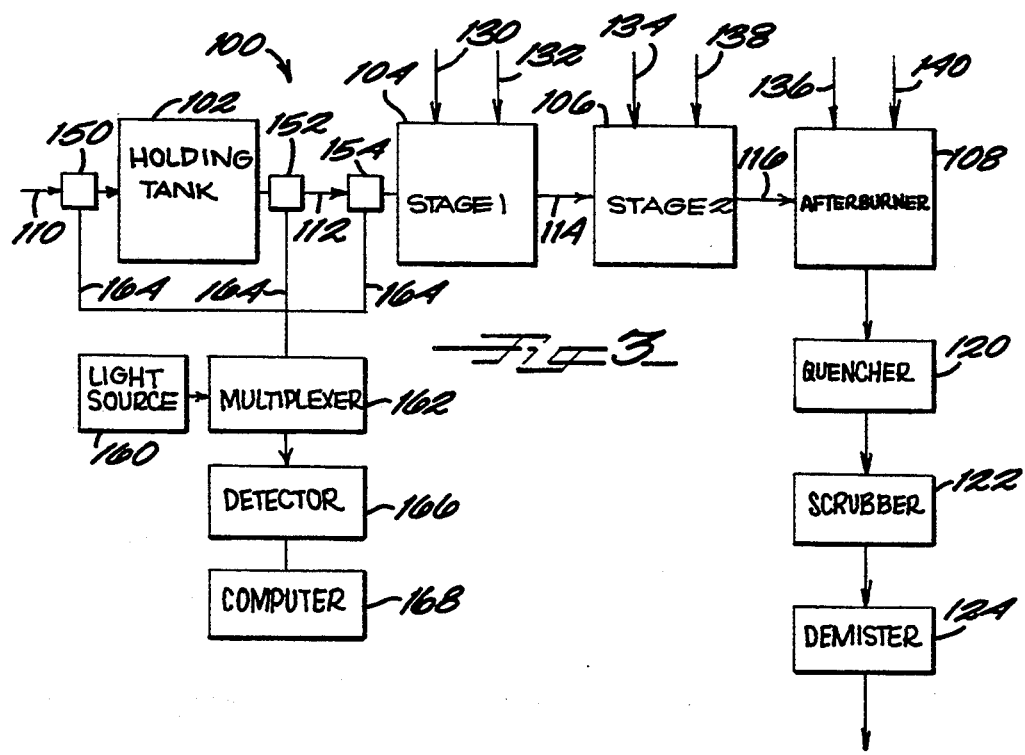
FIG. 3 is a schematic view of a destruction facility having apparatus for implementing the method.

FIG. 3 illustrates use of the present invention in a destruction facility 100. Facility 100 includes a holding tank 102 and a continuous liquid stream incinerator having a first stage 104, a second stage 106 and an afterburner 108. Alternatively, facility 100 may have some other type of incinerator, such as a rotary incinerator or an infrared incinerator, or some other type of process for materials destruction.

Material to be destroyed is transported to facility 100 and fed to holding tank 102 via input line 110. Conduits 112, 114 and 116 connect tank 102 and first stage 104, first stage 104 and second stage 106, and second stage 106 and afterburner 108, respectively.

Facility 100 may include emissions control devices such as a quencher 120, a scrubber 122, a demister 124, and other devices such as Venturi irrigators, filters, cyclone separators and heat exchangers for treating the off-gas from afterburner 108. Fuel (if needed) and combustion gas are supplied to first stage 104 by fuel and air supply lines 130, 132, respectively. Similarly, fuel and air are supplied to second stage 106 and afterburner 108 by fuel lines 134, 136 and air lines 138, 140.

From holding tank 102, the material is conveyed to first stage 104 by conduit 112, where the material is heated and at least partly incinerated and discharged to second stage 106 via conduit 114. Solid combustion products from second stage 106 are discharged into an ash collector (not shown), and volatile combustion products are conveyed to afterburner 108 via conduit 116. Afterburner 108 ensures virtually complete combustion of substantially all combustible gases emitted from second stage 106. Any particulates, volatile organics, and so forth in the off-gas from afterburner 108 are removed by emissions control devices 120, 122 and 124.

Facility 100 may have several points where materials may be diverted and replaced by simulants or surrogates, including but not limited to the points at which material is input to holding tank 102, and transferred from holding tank 102 to first incinerator stage 104. Therefore, facility 100 may include a sensor 150 positioned at the inlet to holding tank 102, a sensor 152 at the outlet of holding tank 102, and a sensor 154 at the inlet to stage 104. Sensor 154 is preferably integrally fashioned with the inlet, so that it is substantially impossible to prevent materials flowing past sensor 154 from entering stage 104. Sensors 150 and 152 are similarly positioned to substantially prevent diversions of materials from facility 10.

Additional sensors may be positioned between stage 104 and stage 106, and between stage 106 and afterburner 108. However, upon entering stage 104, materials are decomposed to the extent that they are no longer useful as, for example, chemical warfare agents. Therefore, such additional sensors are generally not needed for the practice of the invention. Similarly, sensors for process control may be provided as part of facility 100, but are not needed for the practice of the invention.

Light from a source 160 is transmitted to a multiplexer 162. Multiplexer 162 is in optical communication with sensors 150, 152, 154 via a plurality of optical fiber assemblies 164, each assembly 164 having a transmission fiber and a return fiber for transmitting light to and from sensors 150, 152, 154. The output of multiplexer 162 is fed to a detector 166, preferably a spectrophotometer, and a computer 168.

Computer 168 uses stored algorithms to process the digitized information received from detector 166 and determine whether a substance of interest is present in facility 10, and if present, the concentration of the substance. Computer 168 therefore has stored data relating to the spectral signatures of known chemical warfare agents, together with simulants and surrogates of such agents. These known spectra are used in validating facility 10 for the presence of these agents. A typical absorbance spectrum for HD (mustard gas), measured using facility 100, is shown in FIG. 4.

It will be apparent to those skilled in the art that many changes and substitutions can be made to the preferred embodiment herein described without departing from the spirit and scope of the present invention as defined by the appended claims.

What is claimed is:

1. A method for validating a chemical process including reaction of a constituent compound in a reaction vessel, said reaction vessel having an interior and an inlet in communication with said interior, said constituent compound passing through said inlet to said reaction vessel, said constituent compound being altered chemically upon reacting in said reaction vessel, said method comprising the steps of:

directing a light beam into said constituent compound in said inlet just as said constituent compound is entering said reaction vessel;

measuring an optical spectrum of said constituent compound after interaction of said light beam with said constituent compound;

comparing said optical spectrum to a reference spectrum of said constituent compound to determine if said optical spectrum of said constituent compound and said reference spectrum match; and emitting a first signal when said optical spectrum of said constituent compound matches said reference spectrum to confirm said constituent compound is entering said reaction vessel.

2. The method as recited in claim 1, wherein said directing step further comprises the step of positioning a sensor in said inlet, said sensor carrying said light beam to and from said inlet in optic fibers so that said light beam can be directed through said constituent compound near said reaction vessel.

3. The method as recited in claim 1, wherein said directing step further comprises the step of positioning a sensor in said inlet, said sensor having a housing and carrying said light beam into said inlet in a first optic fiber and out of said inlet in a second optic fiber, said second optic fiber being spaced apart from said first optic fiber, said first and said second optic fibers connected to said housing, said housing having a hole through which said constituent compound can pass, crossing said light beam as said light passes from said first to said second optic fiber.

4. The method as recited in claim 1, wherein said method further comprises the steps of:

comparing said optical spectrum to a reference spectrum of a surrogate compound to determine if said optical spectrum of said constituent compound matches said reference spectrum of said constituent compound or said reference spectrum of said surrogate compound; and emitting a second signal when said optical spectrum of said constituent compound matches said reference spectrum of said surrogate compound to alert that said surrogate compound is entering said reaction vessel rather than said constituent compound.

5. The method as recited in claim 1, further comprising continually measuring optical spectra of said constituent compound and comparing said optical spectra to said reference spectrum.

6. The method as recited in claim 1, wherein said measuring step further comprises measuring an absorption spectrum of said constituent compound after said light beam passes through said constituent compound.

7. The method as recited in claim 1, wherein said measuring step further comprises measuring a Raman spectrum of said constituent chemical compound.

8. A method for validating a chemical destruction of a hazardous chemical compound in a reaction vessel, said reaction vessel having an interior and an inlet in communication with said interior, said hazardous chemical compound passing through said inlet to said reaction vessel, said hazardous chemical compound being rendered no longer hazardous upon reacting in said reaction vessel, said method comprising the steps of:

directing a light beam into said hazardous compound in said inlet just as said hazardous chemical compound is entering said reaction vessel;

measuring an optical spectrum of said hazardous chemical compound after interaction of said light beam with said hazardous chemical compound;

comparing said optical spectrum to a reference spectrum of said hazardous chemical compound to determine if said optical spectrum of said hazardous chemical compound and said reference spectrum match; and emitting a first signal when said optical spectrum of said hazardous chemical compound matches said reference spectrum to confirm said hazardous chemical compound is entering said reaction vessel.

9. The method as recited in claim 8, wherein said directing step further comprises the step of positioning a sensor in said inlet, said sensor carrying said light beam to and from said inlet in optic fibers so that said light beam can be directed into said hazardous chemical compound near said reaction vessel.

10. The method as recited in claim 8, wherein said directing step further comprises the step of positioning a sensor in said inlet, said sensor having a housing and carrying said light beam into said inlet in a first optic fiber and out of said inlet in a second optic fiber, said second optic fiber being spaced apart from said first optic fiber, said first and said second optic fibers connected to said housing, said housing having a hole through which said hazardous chemical compound can pass, crossing said light beam as said light passes from said first to said second optic fiber.

11. The method as recited in claim 8, wherein said method further comprises the steps of:

comparing said optical spectrum to a reference spectrum of a surrogate compound to determine if said optical spectrum of said hazardous chemical compound matches said reference spectrum of said hazardous chemical compound or said reference spectrum of said surrogate compound; and emitting a second signal when said optical spectrum of said hazardous chemical compound matches said reference spectrum of said surrogate compound to alert that said surrogate compound is entering said reaction vessel rather than said hazardous chemical compound.

12. The method as recited in claim 8, further comprising continually measuring optical spectra of said hazardous chemical compound and comparing said optical spectra to said reference spectrum.

13. The method as recited in claim 8, wherein said measuring step further comprises measuring an absorption spectrum of said hazardous chemical compound after said light beam passes through said hazardous chemical compound.

14. The method as recited in claim 8, wherein said measuring step further comprises measuring a Raman spectrum of said hazardous chemical compound.

15. A method for validating a chemical process for making a product in a facility having a reaction vessel with an interior and an inlet, said inlet being in fluid communication with said interior, said chemical process using a constituent compound, said constituent compound passing through said inlet into said reaction vessel where said constituent compound is altered chemically upon reacting in said reaction vessel, said method comprising the steps of:

directing a light beam into said constituent compound in said inlet just as said constituent compound is entering said reaction vessel;

measuring an optical spectrum of said constituent compound after interaction of said light beam with said constituent compound;

comparing said optical spectrum to a reference spectrum of a hazardous compound to determine if said optical spectrum of said constituent compound matches said reference spectrum; and emitting a first signal when said optical spectrum of said constituent compound matches said reference spectrum to alert that said hazardous compound is entering said reaction vessel.

16. The method as recited in claim 15, wherein said directing step further comprises the step of positioning a sensor in said inlet, said sensor carrying said light beam to and from said inlet in optic fibers so that said light beam can be directed into said constituent compound near said reaction vessel.

17. The method as recited in claim 15, wherein said directing step further comprises the step of positioning a sensor in said inlet, said sensor having a housing and carrying said light beam into said inlet in a first optic fiber and out of said inlet in a second optic fiber, said second optic fiber being spaced apart from said first optic fiber, said first and said second optic fibers connected to said housing, said housing having a hole through which said constituent compound can pass, crossing said light beam as said light passes from said first to said second optic fiber.

18. The method as recited in claim 15, wherein said method further comprises the steps of:

comparing said optical spectrum to a reference spectrum of a surrogate compound to determine if said optical spectrum of said constituent compound matches said reference spectrum of said hazardous compound or said reference spectrum of said surrogate compound; and emitting a second signal when said optical spectrum of said constituent compound matches said reference spectrum of said surrogate compound to alert that said surrogate compound is entering said reaction vessel rather than said hazardous compound.

19. The method as recited in claim 15, further comprising continually measuring optical spectra of said constituent compound and comparing said optical spectra to said reference absorption spectrum.

20. The method as recited in claim 15, wherein said measuring step further comprises measuring a spectrum selected from the group consisting of absorption spectra and Raman spectra.

* * * * *